(12) United States Patent
Sudmann

(10) Patent No.: US 7,875,083 B2
(45) Date of Patent: Jan. 25, 2011

(54) PROSTHETIC ELEMENT

(76) Inventor: Einar Sudmann, P.O. Box 464, Voss (NO) 5703

( * ) Notice: Subject to any disclaimer, the term of this patent is extended or adjusted under 35 U.S.C. 154(b) by 0 days.

(21) Appl. No.: 11/574,673

(22) PCT Filed: Sep. 7, 2005

(86) PCT No.: PCT/NO2005/000322

§ 371 (c)(1),
(2), (4) Date: Mar. 7, 2007

(87) PCT Pub. No.: WO2006/028382

PCT Pub. Date: Mar. 16, 2006

(65) Prior Publication Data

US 2007/0233243 A1     Oct. 4, 2007

(30) Foreign Application Priority Data

Sep. 8, 2004   (GB) .................................. 0419961.8

(51) Int. Cl.
*A61F 2/36* (2006.01)
(52) U.S. Cl. ................................ 623/23.29; 623/23.44
(58) Field of Classification Search ... 623/23.15–23.38, 623/23.29, 23.31, 23.3, 23.44, 23.34, 23.35, 623/23.5, 20.34, 20.36, 16.11; 606/85
See application file for complete search history.

(56) References Cited

U.S. PATENT DOCUMENTS

| 4,623,353 | A |   | 11/1986 | Buechel |              |
|-----------|---|---|---------|---------|--------------|
| 4,713,076 | A | * | 12/1987 | Draenert | ........... 623/23.6 |
| 5,015,817 | A |   | 5/1991  | Kranz   |              |
| 5,092,899 | A | * | 3/1992  | Forte   | ........... 623/23.32 |
| 5,163,964 | A |   | 11/1992 | Lazzeri |              |
| 5,330,536 | A |   | 7/1994  | Tager   |              |
| 5,976,137 | A | * | 11/1999 | Mayer   | ........... 606/62 |
| 6,187,012 | B1|   | 2/2001  | Masini  |              |
| 2001/0039454 | A1 |   | 11/2001 | Ricci |              |
| 2004/0024469 | A1 | * | 2/2004  | Ferree | ........... 623/23.26 |
| 2005/0021151 | A1 | * | 1/2005  | Landis | ........... 623/23.63 |

FOREIGN PATENT DOCUMENTS

CN      1229778      3/1998

(Continued)

OTHER PUBLICATIONS

Translation of DE3324103.*

*Primary Examiner*—David H Willse
*Assistant Examiner*—Megan Wolf
(74) *Attorney, Agent, or Firm*—Christian D. Abel

(57) ABSTRACT

The invention concerns a prosthetic element (1) with an outer surface defining an interface to the surrounding bone or fibrous tissue, wherein the prosthetic element (1) is provided with at least one internal anchoring cavity (6) for the growing of tissue and a least one guide means (5) for a cutting tool. The guide means (5) and the anchoring cavities (6) are positioned essentially within the perimeter/circumference of the prosthetic element (1) defined by the outer surface of the prosthetic element (1). The anchoring cavities (6) and the guide means (5) are interconnected and at least one of the anchoring cavities (6) and/or the guide means (5) has an opening in the outer surface for the growing of tissue into the element (1).

12 Claims, 8 Drawing Sheets

FOREIGN PATENT DOCUMENTS

| | | |
|---|---|---|
| DE | 3704089 | 8/1958 |
| DE | 3324103 | 11/1984 |
| EP | 0078888 | 7/1982 |
| EP | 0177226 | 4/1986 |
| EP | 0181586 | 5/1986 |
| EP | 0906751 | 4/1999 |
| EP | 0978262 | 2/2000 |
| FR | 2810232 | 12/2001 |
| GB | 2154225 | 9/1985 |
| JP | 09124384 | 5/1987 |
| NO | 20031167 | 3/2003 |
| WO | WO 99/04734 | 2/1999 |
| WO | WO 01/70012 | 9/2001 |
| WO | WO 02/096324 | 12/2002 |
| WO | WO2004/067679 | 8/2004 |
| WO | WO2004/080156 | 9/2004 |

* cited by examiner

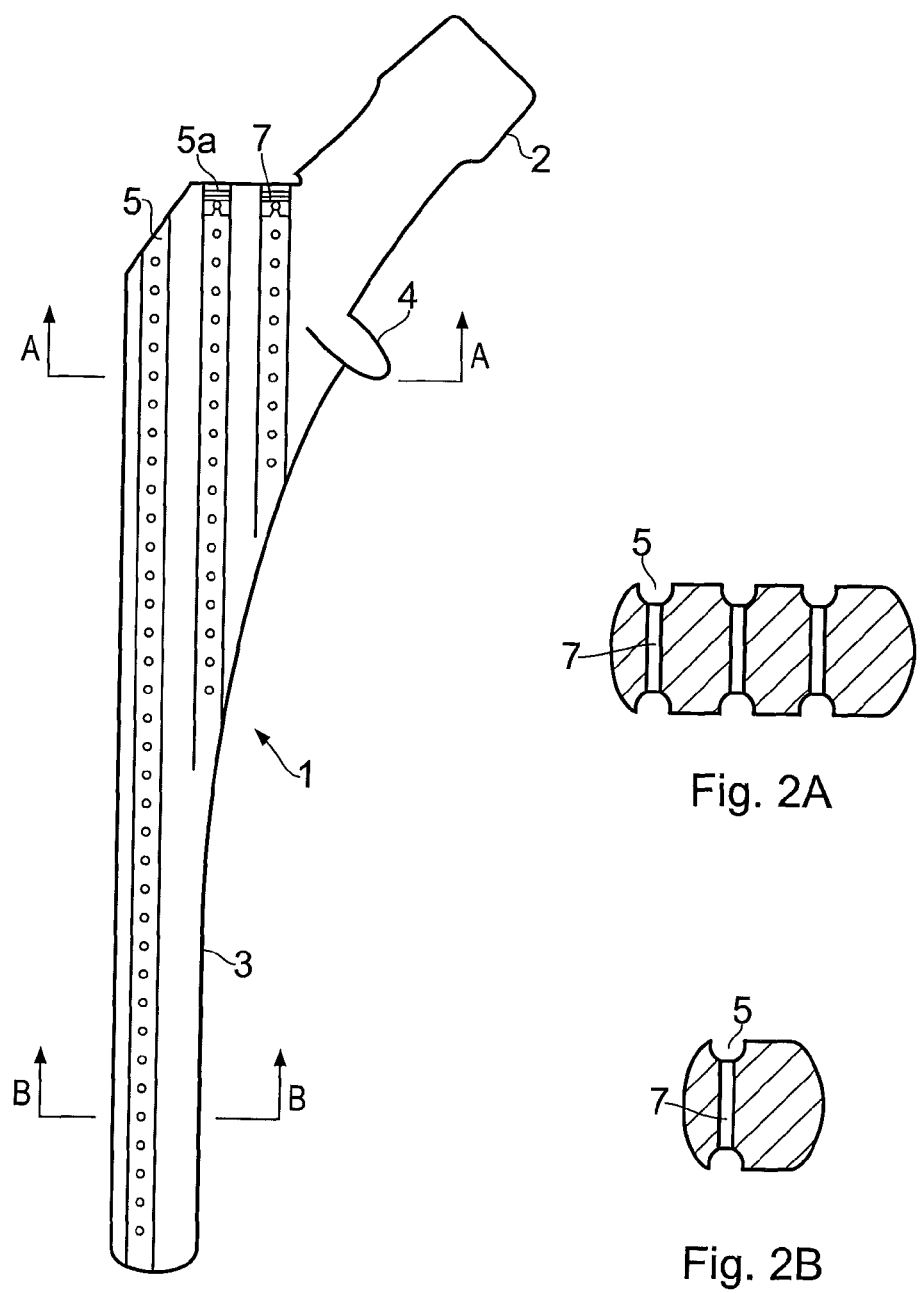
Fig. 2
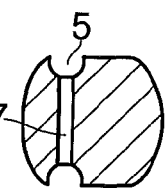
Fig. 2A
Fig. 2B

PROSTHETIC ELEMENT

FIELD OF THE INVENTION

This invention relates generally to a prosthetic element. The prosthetic element according to the invention is applicable in joint-replacement surgery, wherein methods for the anchorage of the prosthetic element to living tissue like bone to be utilized. The configuration of the prosthetic element, according to the invention, facilitates the removal of the prosthetic element if deemed necessary.

BACKGROUND OF THE INVENTION

Prosthetic elements, like joint-replacement surgery in larger synovial joints like the hip, knee or the shoulder, can be anchored to the bone either by bone cement, or by cementless fixation like press fit, or anchorage by fibrous and bone ongrowth, or ingrowth in pores. As for now, fixation with bone cement has given the best long-term results both in the elderly as well in younger patients. Consequently, more cementless elements than cemented ones have been removed and subsequently the need for adequate replacement surgery is essential.

For successful replacement surgery it is deemed necessary to preserve as much bone stock as possible. Thus, ideally, a cementless prosthetic element should permit suitable, rigid anchorage to living tissue, like bone, and in addition, be designed so that it can be retrieved without waste of the living tissue stock needed for successful replacement surgery. The object of the present invention is to fulfill these requirements.

Cementless fixation with prosthetic elements having a plurality of indented or raised portions, provided bone ongrowth, may give good fixation to the bone like the femur. Consequently, such elements may be quite difficult to retrieve. However, such indented or raised portions cannot hinder micro-motion at the element/tissue interface. As the micro-motions causes the patients pain on walking, there is a present need for eliminating or at least minimizing these micro-motions. Moreover, such instability leads to undesirable bone remodeling. Such designs have therefore given poor results in patients.

Replacement of the prosthetic element is necessary in many occasions. Statistics have shown that such revisions have been made in a number of 1 to 6 in relation to primary operations. This illustrates the demand of finding good solutions for removing such prosthetic elements.

Precision press fit of prosthetic elements, like a hip stem, may give good anchorage to bone provided bone tissue ongrowth to a rough surface. The more rough the surface, the better the anchorage. But the more rough the surface, the more difficult the retrieval. Thus, the retrieval of a rough-surfaced element can be very cumbersome. And loss of essential bone stock is inevitable.

Several means have been proposed for the anchorage of the prosthetic element to bone by bone ingrowth. One of these methods involves the application to a portion of the surface of the implant, such as a hip implant, of a coating of sintered balls.

The aim of this method is to provide surface porosity to encourage bone ingrowth. Such a method has several disadvantages like adversely affecting the properties of the material, difficulties to control the surface geometry of the ball coated implant, and surface balls can migrate from the implant causing severe third body wear in the artificial joint proper. Further, the removal of a totally ball coated hip or shoulder joint stem can be disastrous; even if a major part of the bone is temporarily removed, there is the risk of breaking the bone in several pieces.

Mesh pads on a portion of the implant have also been used for anchorage in inventions like U.S. Pat. No. 4,406,023 of Sep. 2. 1983, William H. Harris inventor, and U.S. Pat. No. 4,536,894 of Aug. 27. 1985, Jorge O. Galante et al. inventors. Like sintered balls, these mesh pads give good anchorage. Although a collar obstructing the access to the stem below is provided only medially in the above inventions, removing such implants can be very difficult. And loss of essential bone stock is inevitable.

Austin More designed his cementless hemi prosthetic implant for fractured neck of the femur with a smooth surface facilitating both insertion and possible retrieval. To obtain proximal load transfer a collar was provided. And there are two quite large openings in the stem for bone block anchorage. But such anchorage cannot hinder undesirable micro-motion at the bone/tissue interface. Moreover, to retrieve such prosthesis the anchoring bone blocks have to be removed either by a saw or using a chisel. A collar naturally obstructs the access to the stem below. Thus, to remove the anchorage a quite large access may be needed, the larger the more loss of bone stock.

To obtain more bony anchorage than the above Austin More design patent U.S. Pat. No. 5,330,536 Femur portion of a hip, Jul. 19, 1994, Karl H. Täger and Hans E. Harder inventors, adds multiple Austin More-type-holes to a hollow prosthesis. Naturally, the more anchoring holes the better the fixation, but the more difficult the retrieval if deemed necessary. Provided the interior of the stem is packed with bone tissue, anchorage by bone ingrowth through these quite large holes may be induced. The hollow space, extending from the upper to lower part of the prosthesis, is conical tapering distally so to aid compressing, from above, to the spongy tissue filled therein. The object of this invention is to "design an effective configuration for the stem of a hip joint prosthesis by which the charging with spongy material is facilitated". Although some of this spongy material might be removed from the hollow space of the prostheses, this procedure alone does not loosen the prosthesis sufficiently to be able to remove the prosthesis from the femur. The removal of such prosthesis involves cutting bone material loose from prosthesis by an extensive approach to the outside of the prosthesis. This operation has features similar to the method used for the totally ball coated stem described above, and results in a relatively extensive loss of bone stock.

For proximal load transfer a collar may be desirable. U.S. Pat. No. 4,623,353 discloses a stem-type femoral prosthesis including a collar provided with access slots for resectioning means, Nov. 18. 1986, Fredrick F. Buechel and Michael J. Pappas inventors, have therefore provided one access slot on each side of a collar. This access slot gives access to the proximal part of the stem, but using a saw or chisel onto the outside of a prosthetic element will inevitably lead to loss of bone stock. Moreover, the slots above give access to the uppermost part of the stem only.

The invention EP 0078 888 Gerader, blattartiger Schaft für eine Gelenkendoprothese, Jul. 24. 1982, Maurice E. Müller inventor, was designed without a collar obstructing the access to the quite large Austin-More-type-holes in the stem for anchoring bone blocks. To reduce the problems of retrieval somewhat this invention also includes a shallow, longitudinal gutter partly guiding the chisel along the implant when hammering off the anchorage. However, as outlined above, such large bone block anchorage cannot hinder undesirable micro-mobility at the implant/bone interface. Second, on retrieval, the chisel (or saw), inevitable destroys bone stock. The more distal the cutting, the more bone stock loss. If not, the femur will crack.

U.S. Pat. No. 6,187,012 B1 a prosthetic element removal apparatus and methods, Feb. 13, 2001, Michael A. Masini inventor, incorporates a "guide means direct a cutting tool into the interface between a prosthesis and surrounding bone to bring about a more controlled separation thereof for revision or other purposes." This guide means might be on the outside of the prosthesis, or located in the vicinity of the outside of the prosthesis as externally open, semicircular, parallel gutters with an opening in the outside surface of the prosthesis. These guides must be parallel and straight, or the external cutting tool will be stuck. So these guides can only be used in the upper part of a curved prosthetic element. And as outlined above, using a cutting tool into the interface between prosthesis and the surrounding bone will inevitably lead to loss of bone stock, or the bone will crack.

EP 181586 concerns a prosthetic element comprising a prosthetic main part provided with projecting ribs distributed around the circumference of the prosthetic main part. The ribs extend in the longitudinal direction along an upper portion of the prosthetic main part. Several through holes are formed in the ribs for the ingrowth of bone tissue. A possible removal of the prosthetic element would cause considerable loss of bone. The space between the longitudinal ribs may provide some guidance for the cutting tool, but the shape of these spaces does not provide protection so as to minimize the loss of bone stock. Further, each outer edge of the ribs is cogged and the distal portion of the prosthetic element has plural structures to ensure the fixation of the prosthetic element. As the overall design indicates the intention of the prosthetic element is to provide a prosthesis which ensures a reliable fixation to the femur, while the easy removal of the prosthesis has been no object of the invention of EP 181566.

Several means have been proposed for anchoring cementless prosthetic elements, and, as outlined above, some few for facilitating their retrieval. But the better the anchorage, the more difficult the retrieval. And retrieval of the above prosthetic designs inevitable lead to loss of bone stock, or the bone will break in two or more pieces, or both. Such alternatives are undesirable. In contrast, the present invention seeks to provide implants avoiding such serious complications on retrieval.

SUMMARY OF THE INVENTION

The object of present invention is to provide a prosthetic element having a configuration which permits anchorage to living tissue like bone and which minimizes the problems associated with the retrieval of the prosthetic element. This object is achieved in accordance with the independent claim 1 and the embodiments of the invention defined in the following dependent claims.

The prosthetic element according to the invention may be used for various orthopedic replacements within the body of man or animal. The prosthetic element may be utilized for reconstructions in the skeleton, for larger synovial joints of the lower and upper extremity for instance the hip, knee, shoulder and elbow etc. Alternatively the prosthetic element may function as an implant in the oral cavity.

Although primarily designed for cementless fixation of artificial joints in man or in animals like dogs, or as anchoring devices for artificial teeth, the implants may, if deemed necessary for other reasons, be fixed by bone cement, except when designed for the ingrowth of fibrous tissue only (FIG. 3).

The prosthetic element has an outer surface defining an interface to the surrounding bone or fibrous tissue, wherein the prosthetic element is provided with at least one internal anchoring cavity for the growing of tissue and a least one guide means for a cutting tool.

Guide elements for a cutting tool are shown in U.S. Pat. No. 6,187,012. As opposed to the invention these guide elements are provided for guiding the cutting tool to perform the cutting operation on the outside of the prosthetic element, whereas the cutting operation for the loosening of the prosthetic element according to the current invention is performed inside the prosthetic element as described above.

The spaces between the ribs of the prosthetic element disclosed in EP 181 586 may be perceived as guide elements for the cutting tool. As for the prosthetic element of U.S. Pat. No. 6,187,012, the prosthetic element of EP 181 586 requires access from the outside of the prosthetic element to be removed. The spaces between the ribs of EP 181 586 and guide elements are not positioned within the prosthetic element.

The outer surface of the prosthetic element in accordance with the invention is preferably smooth to facilitate the retrieval of the prosthetic element if deemed necessary.

The anchorage of the prosthetic element is provided by ingrowth of fibrous or bone tissue, or both, in the anchoring cavities that may be constituted by conventional holes or pores, of any geometrical shape inside the prosthetic element. In contrast to conventional holes or pores, however, the anchoring cavities are all oriented and connected to one or more of the guide means so that the anchorage to periprosthetic tissue, on retrieval, can be removed by a suitable cutting tool.

Anchoring cavities may be constituted by holes, slits, gutters, channels, pores or micro-pores or other cavities enabling ingrowth of tissue into the prosthetic element. Bone anchorage is best obtained when the diameter of the holes or pores are greater than 0.25 mm, and the prosthetic element is made of a material favoring bone ongrowth like titanium. To exclude bone in favor of fibrous tissue ingrowth the maximum diameter of pores should preferably be less than 0.1 mm, and the prosthetic element made of a material favoring fibrous tissue encapsulation like stainless steel.

The guide means and the anchoring cavities are positioned essentially within the perimeter/circumference of the prosthetic element defined by the outer surface of the prosthetic element. The anchoring cavities and the guide means are interconnected and at least one of the anchoring cavities and/or the guide means has an opening in the outer surface for growing of tissue into the element. Thus, the guide elements and/or anchoring cavities may be positioned proximate or deep to the outer surface.

By positioning the guide means within the prosthetic element, and interconnecting the guide means with the anchorage cavities, the cutting of tissues to be able to remove the prosthetic element, takes place essentially within the prosthetic element. The bone stock surrounding the prosthetic element is thereby given an improved protection due to the positioning of the guide means. Compared to prior art as cited above, the need for removing bone stock surrounding the prosthetic element to get access to the outer surface is eliminated or minimized. Consequently, the loss of bone stock is to be reduced when removing a prosthetic element in accordance with the invention.

The positioning of the guide elements and the anchorage cavities within the prosthetic element, and the interconnection between these two, produce a synergistic effect of good anchorage and the possibility of easy removal of the prosthetic element.

The guide means may assume various shapes to fulfill the purpose of enabling a cutting tool to remove essentially ingrown, anchoring tissue in pores or holes without compromising periprosthetic tissue stock. The guide means may be shaped like grooves, recesses, hollows, gutters, channels or tunnels etc for the insertion of the cutting tools. Further, the cross section of the guide means may be spherical, semispherical or assume any other suitable form. The shape and/or the dimension of cross sections of the guide means may be uniform or vary along the longitudinal direction of guide means. The guide means may for instance have a circular cross section in the proximal part of the prosthesis element, whereas the cross section in the distal part is slightly more than semicircular (or semicircular).

In the particular case of a stemmed prosthesis such as a proximal femoral component, the invention preferably provides one or more guide means longitudinally all along, or to a portion of, the polished stem of the implant. These guide means are preferably designed so that the cutting tool like a stiff, or particularly a flexible drill bit, cannot go astray. In this respect also the collar of the stem may be provided with holes guiding a bore exactly to the guide means of the stem.

The anchoring cavities are oriented with an angle to the guide means, preferably perpendicular to the guide means. Preferably, the guide means extend in the longitudinal direction of the element and the anchoring cavities extend in the transverse direction of the element In one embodiment the anchoring cavities extend both in the longitudinal and the transverse direction of the element and have a longitudinal opening in the outer surface of the prosthesis element. The number of guide means and anchoring cavities and their extension in the longitudinal and transverse direction respectively, is to be varied dependent on the conditions of the various fields of appliance. The cavities do not necessarily extend from one guide means to the opposite positioned guide means.

In one embodiment of invention the guide means are positioned close to the outer surface of the element, each guide means having one longitudinal opening in the outer surface, for instance coincidently with the circumference of the prosthetic element. When guiding the cutting tool in the guide means for cutting purposes this may to some extent effect the bone stock surrounding the prosthetic element, as the cutting tool is not entirely separated from the bone stock in accordance with this embodiment. Even so, the loss of bone stock when applying this embodiment is considerably reduced compared with prior art. If necessary the impact of the cutting tool on bone stock may be reduced by positioning the guide elements further away from the circumference.

The upper end of these guide means may be threaded so that a suitable, short screw can close them. The threaded part may also be used for anchorage of a suitable instrument for the insertion or the removal of the prosthesis. According to a special embodiment the whole guide means may be formed as a thread in order to functions as a fastening surface.

According to an alternative embodiment no cavities are provided between the guide means. Instead the surface or a part of the surface inside the guide means may be provided with a layer of a porous material for ingrowth of fibrous or bone tissue.

The prosthetic elements can be made by conventional means or by a Rapid Prototyping and Rapid Manufacturing technique like The Metal Printing Project (MPP), The Electron Beam Melting (EBM) process, or Laser Engineered Net Shaping (LENS). The stem of the prosthetic element may also be curved. This does not lead to any problem when using a flexible bore.

BRIEF DESCRIPTION OF THE DRAWINGS

FIG. 2 is a schematic side-view drawing of a modification of the proximal femoral endoprosthesis shown in FIG. 1, for ingrowth of fibrous or bone tissue in pores or holes extending right through the implant, open to guide means for a cutting tool on opposite sides of the implant.

FIGS. 2A and B are transverse sections of FIG. 2.

DETAILED DESCRIPTION OF THE INVENTION

Although this description focuses on the application of the invention to a proximal femoral prosthesis, the invention is equally applicable to other types of cementless or cemented prosthesis. That is, the cutting guide means may be applied to other types of devices having different geometries.

Figures 1, 1A, 1B:
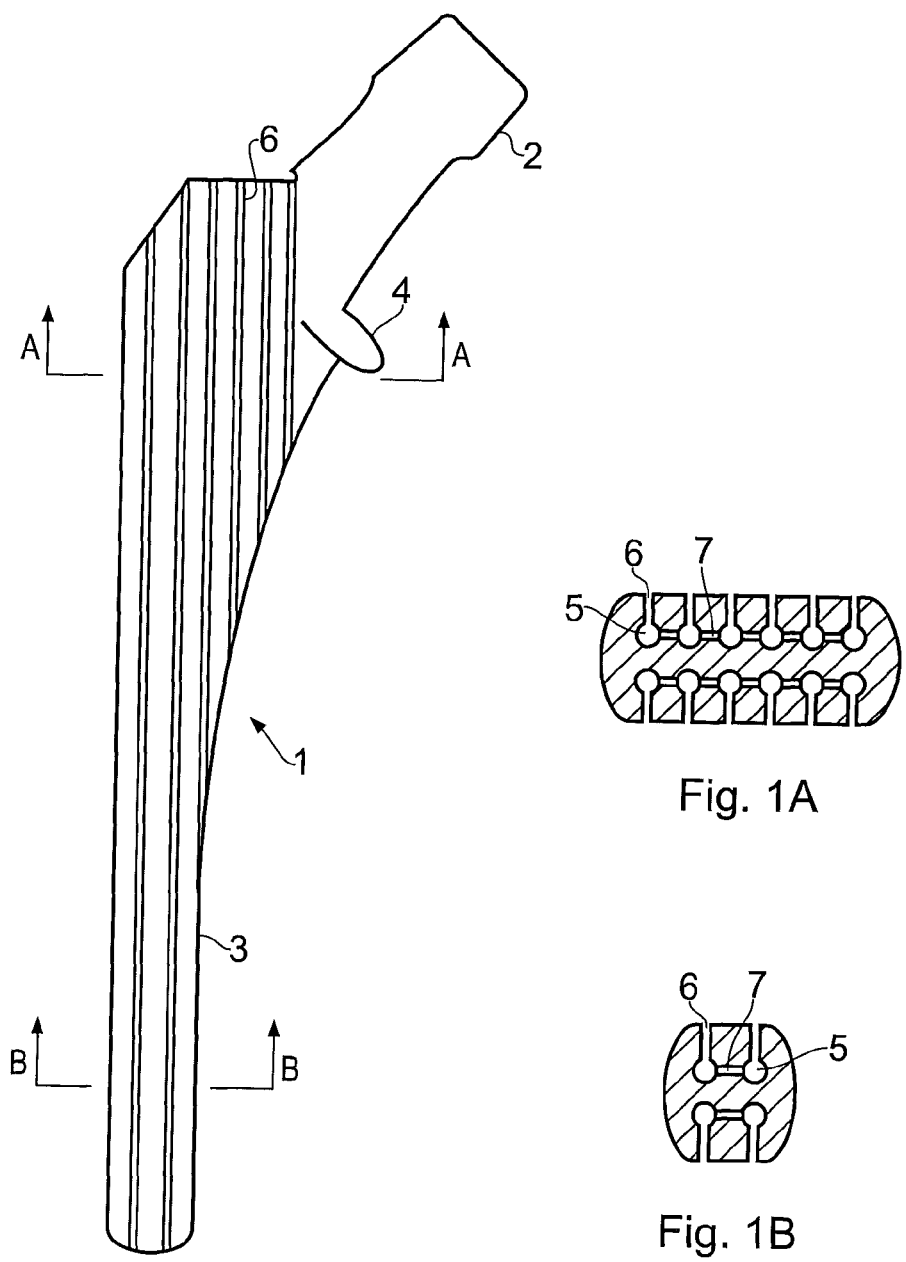
FIG. 1 is a schematic side-view drawing of a proximal femoral endoprosthesis, with a medial collar, for ingrowth of fibrous or bone tissue in pores or holes transversely oriented to longitudinal, externally open, groves or gutters for a cutting tool.
FIGS. 1A and B are transverse sections of FIG. 1.

According to one aspect of the invention as seen in FIG. 1, the prosthesis comprises an elongated stem having a smooth outer surface, a portion of which defines, when the element is implanted in a subject, a contact interface between the stem and surrounding bone and/or fibrous tissue. The prosthesis has one or more longitudinal guide channels located to the interior of the outer surface of the stem, and each of said channel or channels have an at least semi-circular wall portion. The radius of curvature of the at least semi-circular wall portion is adapted for receiving and laterally retaining a drill bit. According to one aspect of the invention the guide channels are longitudinal circular bores 5 arranged in the interior of the stem. A plurality of anchoring cavities 7 adapted for receiving ingrowth of bone or fibrous tissue extend from the at least semi-circular wall portion of one or more of the guide channels.

Each of said longitudinal channels is transversely open to the exterior along substantially its entire length. As seen in FIG. 1 a longitudinal groove 6 is arranged in the surface of the stem exposing the interior of the circular bore 5 to the surrounding tissue. The anchoring cavities and guide channels are mutually arranged such that any ingrowth of bone or fibrous tissue must first enter a guide channel 5 before entering into an anchoring cavity 7. With this arrangement, a drill bit adapted for passing along the length of the guide channels would necessarily sever the ingrown bone or fibrous tissue at the intersection between each anchoring cavity and their respective guide channel, thus allowing the prosthetic element to be removed.

FIG. 1. illustrates a proximal modular type femoral endoprosthesis (1), with a conventional Morse tapered upper end (2) for the ball and a tapered, polished, conical distal end (3). Longitudinally along the stem, several anchorage cavities shown as slits or gutters (6) provide access for fibrous or bone tissue ingrowth. As illustrated in the figure the anchorage cavities may have a longitudinal extension all along the length of the prosthesis or along a portion of the length.

Longitudinal guide means for a cutting tool (5) are located somewhat deep in the stem, outward open by the slit (6) as illustrated in FIGS. 1A-B.

The guide means may also be located quite superficial as illustrated in FIG. 2 in which the shape of the cross section of the guide means (5) preferably is slightly more than semicircular so to hinder a cutting tool to go astray.

A medial collar only (4) is indicated in the drawing. In the case that a full circumferential collar is provided, for proximal load transfer, the guide means goes right through the collar, and such a collar will thus not obstruct a controlled retrieval of the prosthesis.

Figures 4A, 4B, 4C, 4D:
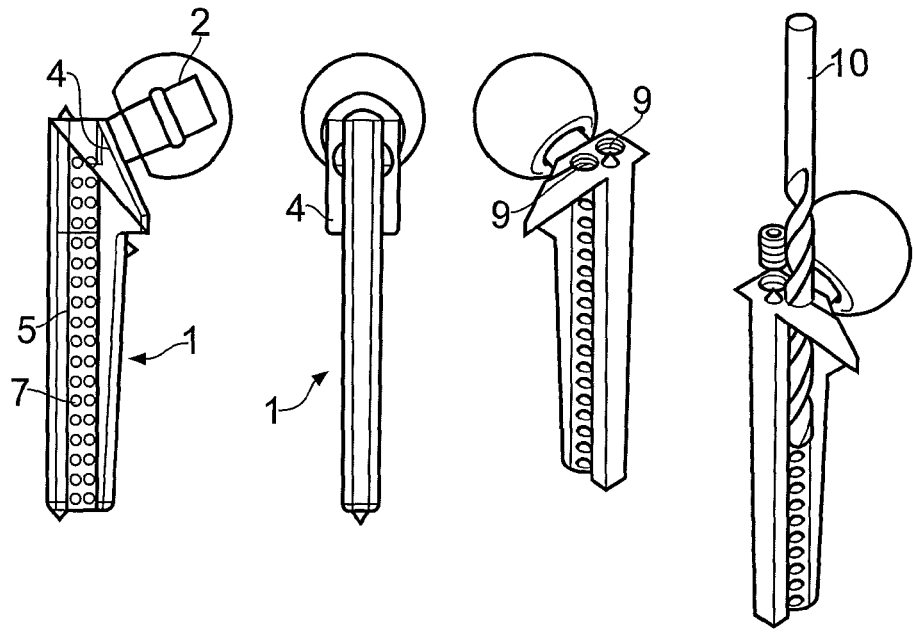
FIGS. 4A-D—four views illustrating a further embodiment of the invention, FIGS. 4C-D showing the positioning of above.

Tissue growing into the guide means (5) is possible directly as shown in FIG. 2A-B or via the slits (6) illustrated in FIG. 1A. Further anchorage, and the most important one, is provided by tissue growth into pores, holes or small channels (7) transversely interconnecting the guide means (5), or holes or pores extending right through the implant from one guide means to one on the other side of the implant (FIGS. 2A-B and 4), or both.

The uppermost end of the guide means may be threaded so that a suitable, short screw can close the guide. An example of the threaded part (5a) is illustrated in FIG. 2. The threaded part (5a) may also be used for anchorage of a suitable instrument for the insertion or the removal of the prosthesis, or a drill guide.

To promote bone ingrowth in the guide means (5), and in particular into the anchoring holes or pores (7), they may be coated by a tissue ongrowth promoting material like hydroxyapatite, or sustained drug release substances as described in U.S. Pat. No. 4,913,903, 1990, inventors Einar Sudmann et al.

As outlined above a prosthetic element may by be anchored to living tissue by tissue ingrowth. Whether anchorage by bone or by fibrous tissue only will give the best long-term results in patients has yet to be decided. However, the very best anchored "implant" in man and animals, the tooth, is anchored by fibrous tissue, by multiple small collagen fibrils. And such anchorage by fibrous tissue only has stood the test of millions of years.

Figure 3A:
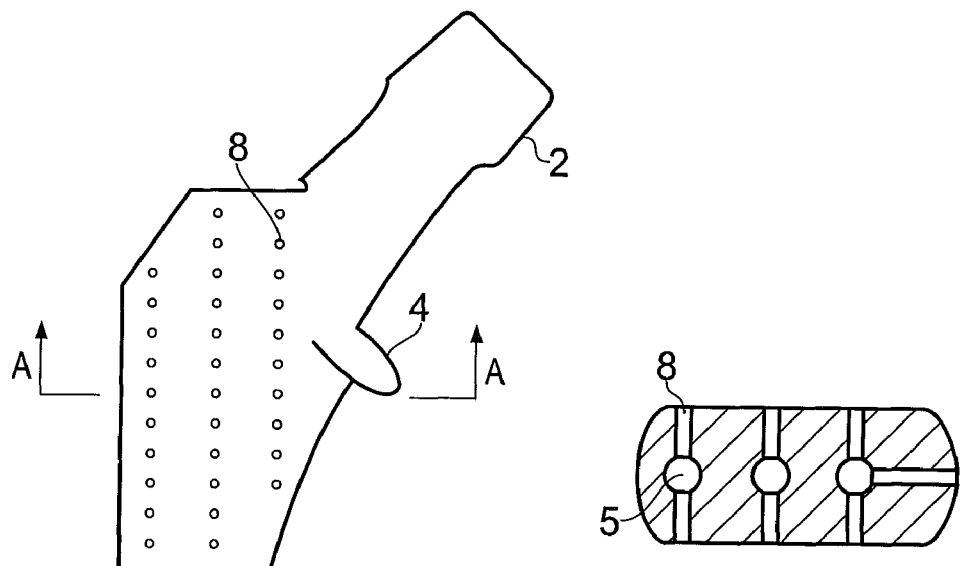
FIGS. 3A, B and C are transverse sections of FIG. 3.
Figure 3B:
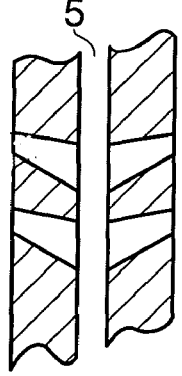
FIG. 3 is a schematic side-view drawing of a proximal femoral endoprosthesis. In the particular case that anchorage is provided by fibrous tissue ingrowth only, the circular guide means for a cutting tool may be located within the stem.
Figure 3C:
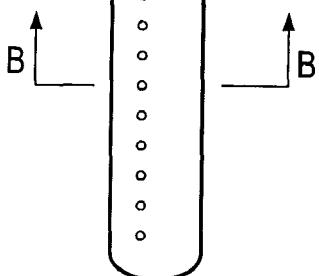
Figure 3:
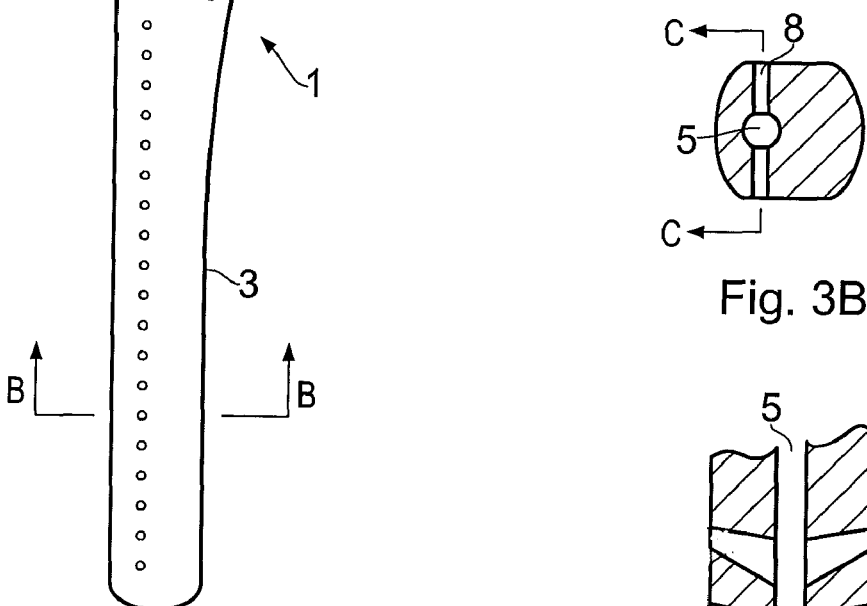
Figure 8:
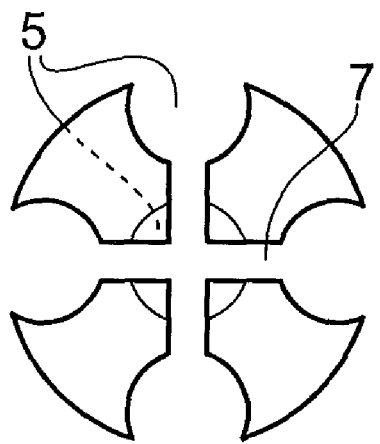
FIGS. 8-9 are schematic transverse drawings of a dental implant serving as anchorage for an artificial tooth.
Figure 9:
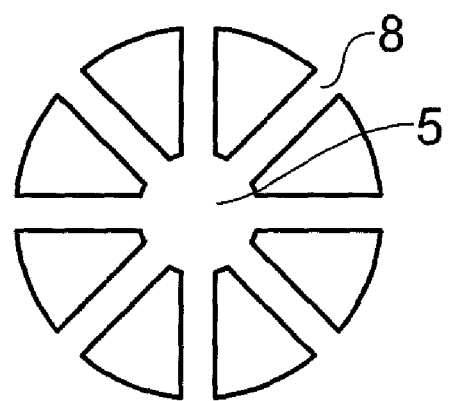

FIG. 3 illustrates a prosthetic implant for fibrous tissue anchorage. As outlined above, to hinder bone tissue ingrowth, pores for fibrous tissue anchorage should preferably have a maximal diameter of less than 0.1 mm. The pores (8) in FIG. 3 are thus not drawn to scale. The essential part is that the pores are oriented perpendicular (FIGS. 3A-B), or at any angle, to the guide means (5) for the cutting tool. The external opening of each pore, or hole (8) may be pointed at the distal perimeter (9) acting as a miniature cutting device, cutting the ingrown tissue therein on retrieval (FIG. 3C, 8-9). FIG. 3A shows an example of plural pores/holes connected to each guide means. In the left portion of the prosthesis element the guide means (5) are connected to through holes (8) running from one side to the other of the prosthesis element, whereas in the right portion of the prosthesis element additional holes are provided in a direction perpendicular to the thickness direction. As the skilled person will understand the configuration of the holes (8) may be performed in various ways.

FIGS. 4A-D describe a further embodiment of the invention. This schematic drawing of a femoral hemiprosthesis (for animals) is in principle of the same type as the embodiment of FIG. 2, but have only one guide means on each side. Between the guide means there are provided cavities or through holes 7. The collar 4 of the prosthesis element has a special design. The upper part has a certain thickness and is provided with holes 9 ending in the respective guide means or channels 5. When the element 1 shall be removed a bore 10 is inserted in the holes 9 and the bore is cutting the anchoring tissues in the cavities 7 as illustrated on FIG. 4D. Then the element can be withdrawn.

Figure 5:
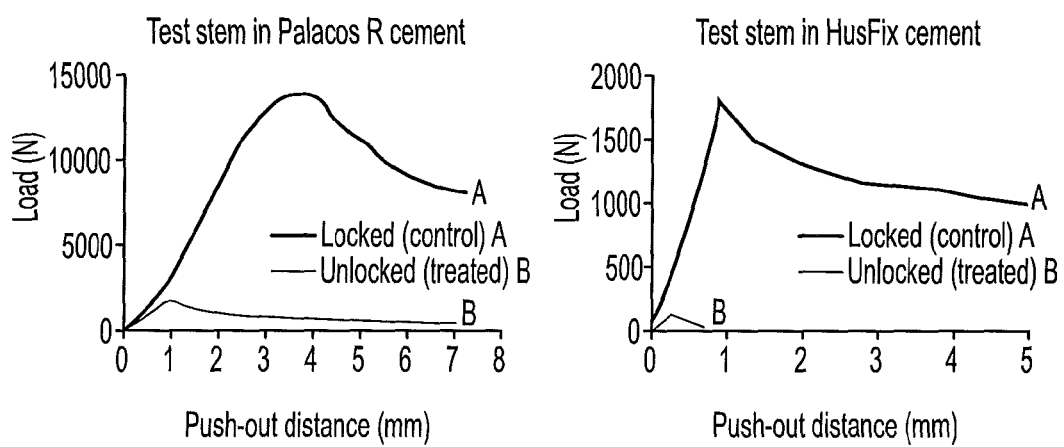
FIG. 5 Diagrams illustrating the effect of the invention when using the embodiment according to a test stem, in principle, designed as FIG. 4.

FIG. 5 illustrates the effect of the invention. The upper curve (A) in the graphs shows the load necessary for push-out/withdrawal of a test prosthetic element, while the lower curve (B) illustrates the markedly reduced load needed after a treatment according to the invention.

Figure 6:
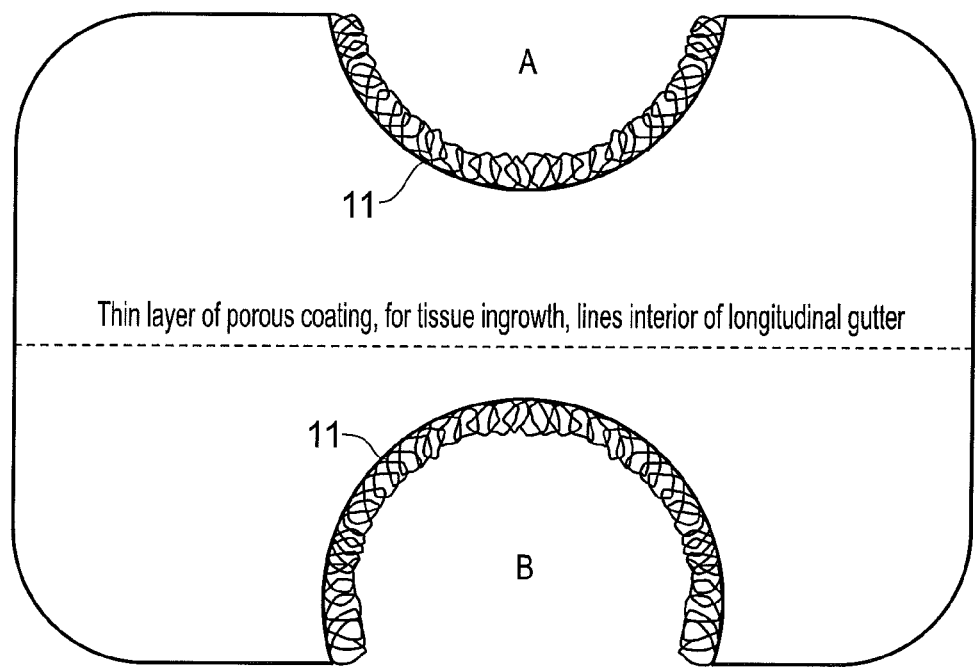
FIG. 6—A sectional view of another embodiment in which the guide gutters are covered by a porous layer (not drawn to scale).

Another embodiment is proposed in FIG. 6. Configurations, for instance as shown in FIGS. 2 or 4, may be constructed without the cavities 7. Instead, at least a part of the inner surface of the guide, means 5 is provided with a layer 11 that is suitable for bone or fibrous tissue ingrowth. The layer may have a thickness of 500µ with communicating pores. The dimension of the pores should be small, for instance less than 100µ, if only ingrowth of fibrous tissue is wanted.

In this way it is possible to achieve a good anchorage by bone and/or fibrous tissue without having through holes, from one side to the other, in a thick element.

Figure 7:
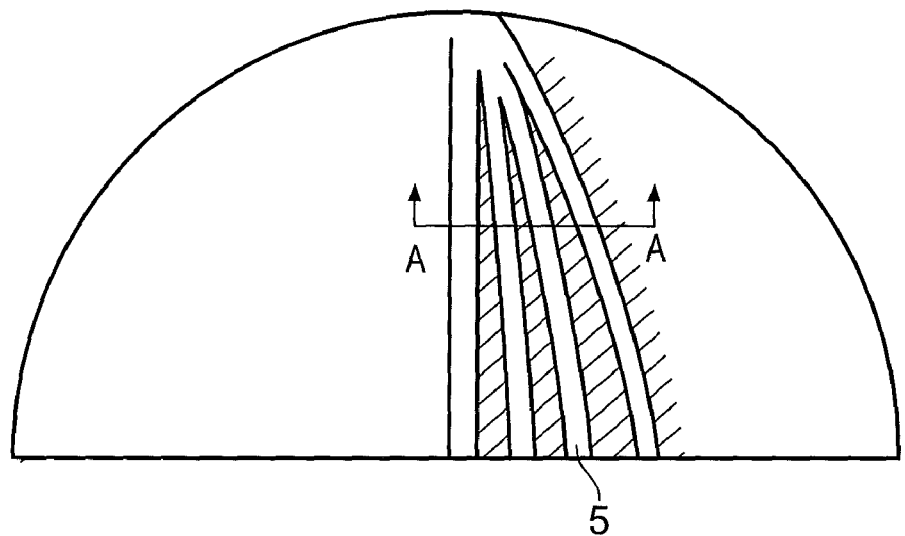
FIG. 7 is a schematic side-view drawing of the outer shell of an acetabular cup.
Figure 7A:
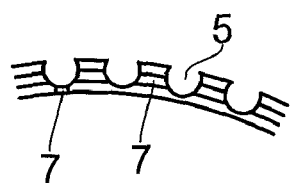
FIG. 7A is a schematic transverse section of FIG. 7.

FIG. 7 illustrates how an acetabular shell for the hip joint liner may be designed. The guide means (5) for a flexible cutting instrument radiate out from the dome, and the anchoring pores or holes (7) interconnect these guide means, or goes right through the shell.

FIG. 8 illustrates a dental implant serving as a base for an artificial tooth. As above anchorage is secured by bone or fibrous tissue, or both, in holes or pores (7) open to longitudinal guide means (5) for a cutting device. The implant may be circular as illustrated, or any desirable shape. The surface is polished, and for primary fixation in the jaw, a circular implant may be formed like a screw.

FIG. 9 illustrates a dental implant serving as a base for an artificial tooth. Anchorage is here, however, provided by fibrous tissue ingrowth in pores (8) as in FIG. 3. The implant may be circular as illustrated, or any desirable shape. The surface is polished, and for primary fixation in the jaw a circular implant may be formed like a screw.

Figure 10:
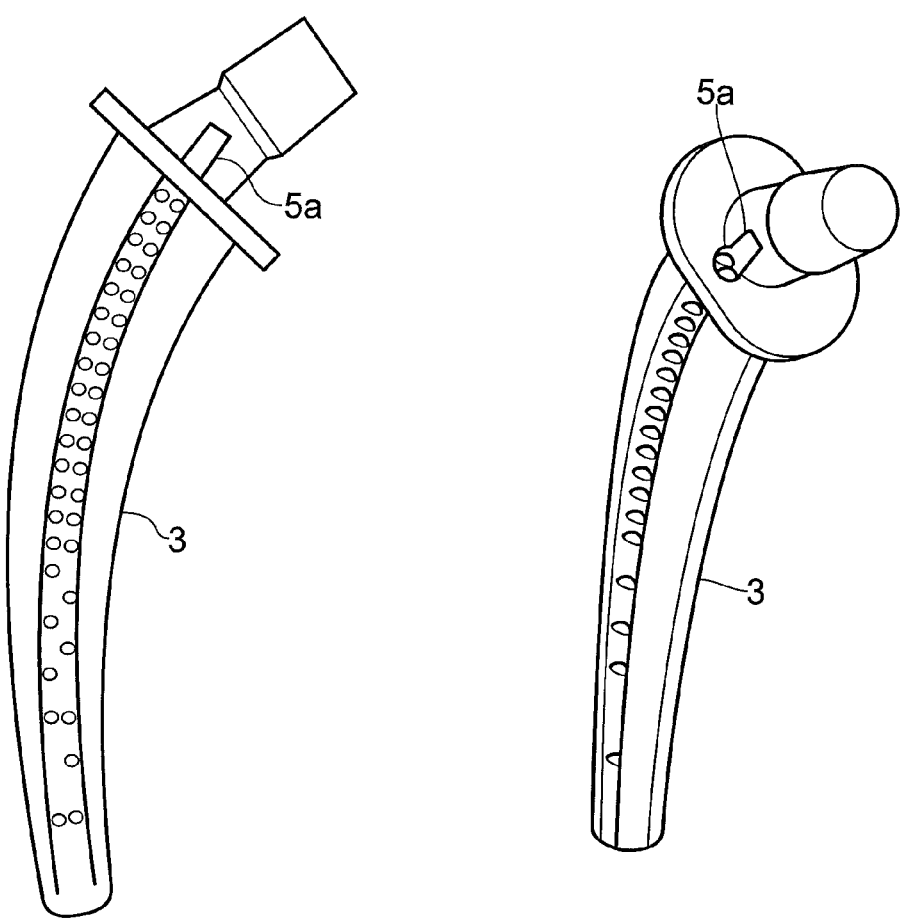
FIG. 10 is an embodiment with a curved femoral stem.

In FIG. 10 there is shown an embodiment with a curved prosthetic element (3). The upper part of the guide means is threaded (5a), like the ones shown in FIG. 2. In this embodiment a flexible bore must be used.

Anchoring pegs in an implant like knee or ankle prosthesis may be designed as illustrated in FIGS. 8-9. These pegs may be conical, circular, oval, or any shape in between, in transverse section. To gain access to the guide means (5) in the peg of a convex component, like a femoral one, it might be necessary to remove a preformed weakened part of the implant.

Many modifications are possible within the scope of the invention. The configuration of guide means and cavities may be modified, as well as their relationship. However, longitudinal threaded guide means, or gutter, 5 mentioned above, will be suitable for anchorage by bone tissue ongrowth only, not by fibrous tissue. The stem may be straight, or conical as shown but the invention will also be suitable by curved stems, using flexible bores.

The invention claimed is:

1. A removable prosthetic element comprising
   an elongated stem having a smooth outer surface, a portion of which defines, when the element is implanted in a subject, a contact interface between the stem and surrounding bone and/or fibrous tissue,
   one or more longitudinal guide channels located to the interior of the outer surface of the stem, each of said channel or channels comprising a longitudinal circular bore having a wall portion arranged in the interior of the stem, the bore being adapted for receiving and laterally retaining a drill bit, and
   a plurality of anchoring cavities adapted for receiving ingrowth of bone or fibrous tissue, all of which extend from the wall portion of one or more guide channels,
   each of said longitudinal channels being transversely open to the exterior along substantially their entire length via a longitudinal groove arranged in the outer surface of the stem, whereby a passage is provided for tissue ingrowth, via the groove, to the interior of the circular bore, and therefrom into the anchoring cavities,
   the anchoring cavities and guide channels being mutually arranged such that any ingrowth of bone or fibrous tissue must first enter a guide channel before entering into an anchoring cavity, whereby a drill bit adapted for passing along the length of the guide channels would necessarily sever the ingrown bone or fibrous tissue at the intersection between each anchoring cavity and their respective guide channel, thus allowing the prosthetic element to be removed.

2. A prosthetic element according to claim 1, wherein the anchoring cavities are passageways connecting adjacent guide channels.

3. A prosthetic element according to claim 1 wherein the stem has an upper surface, said upper surface having through-going circular apertures arranged for providing access for a drill bit through the upper surface to the guide channels.

4. A prosthetic element according to claim 3 wherein the apertures are threaded.

5. A prosthetic element according to any one of claim 1, 2, 3 or 4, wherein the prosthetic element further comprises a collar, said collar having through-going apertures leading to respective channels.

6. A prosthetic element according to claim 1 wherein the prosthetic element is a femoral prosthesis.

7. A prosthetic element according to claim 1 wherein the prosthetic element is a prosthetic implant for fixation of artificial joints in humans or in animals.

8. A prosthetic element according to claim 1 wherein the prosthetic element is an anchoring device for artificial teeth.

9. A method for the subsequent removal of a previously implanted and affixed prosthetic element of the type according to claim 1, comprising the steps of:
   a. examining a patient having a previously implanted prosthetic element of the type according to claim 1, and determining that said prosthetic element should be removed,
   b. at a time of desired removal of the prosthetic element, surgically gaining access to an upper end of the stem,
   c. passing a drill bit along the guide channels so as to sever the anchoring ingrowth of bone or fibrous tissue, and
   d. extracting the prosthetic element, said extraction being facilitated by the smooth outer surface of the stem.

10. A method according to claim 9 wherein the prosthetic element is a femoral prosthesis.

11. A method according to claim 9 wherein the prosthetic element is a prosthetic implant for fixation of artificial joints in humans or in animals.

12. A method according to claim 9 wherein the prosthetic element is an anchoring device for artificial teeth.

* * * * *